United States Patent
Stuttle (12)

(10) Patent No.: US 6,217,846 B1
(45) Date of Patent: *Apr. 17, 2001

(54) SYNTHETIC PEPTIDES FOR USE IN THROMBUS DETECTION

(75) Inventor: Alan William John Stuttle, Hayes (GB)

(73) Assignee: Antisoma Research Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/010,290

(22) Filed: Jan. 21, 1998

Related U.S. Application Data

(63) Continuation of application No. 08/816,922, filed on Mar. 12, 1997, now Pat. No. 5,843,402, which is a continuation of application No. 07/963,127, filed on Oct. 19, 1992, now abandoned, which is a continuation of application No. 07/659,343, filed on Mar. 21, 1991, now abandoned.

(30) Foreign Application Priority Data

Jun. 19, 1989 (GB) .................................................. 8914020
Jun. 18, 1990 (WO) .................................. PCT GB9000933

(51) Int. Cl.[7] .......................... A61K 51/00; A61M 36/14
(52) U.S. Cl. ...................... 424/1.69; 530/331; 424/1.65; 424/1.11
(58) Field of Search ................................. 424/1.11, 1.65, 424/1.69, 9.1, 9.3, 9.4, 9.5; 530/300, 331; 534/7, 10–16

(56) References Cited

U.S. PATENT DOCUMENTS

| | | | |
|---|---|---|---|
| 5,395,609 | * | 3/1995 | Stuttle .................................. 424/1.69 |
| 5,736,122 | * | 4/1998 | Dean et al. .......................... 424/1.69 |
| 5,843,402 | * | 12/1998 | Stuttle .................................. 424/1.69 |

OTHER PUBLICATIONS

Childs, 1985, Optimum Conditions for Labeling of DTPA–Coupled Antibodies with Technetium–99m, *J. Nucl. Med.*, 26(3):293–299.

Hnatowich, et al., 1983, Radioactive Labeling of Antibody: A Simple and Efficient Method, *Science*, 220:613–615.

Paik, et al., 1985, The Labeling of High Affinity Sites of Antibodies with $^{99m}$Tc, *Int. J. Nucl. Med. Biol.*, 12(1):3–8.

Pierschbacher and Ruoslahti, 1984, Cell attachment activity of fibronectin can be duplicated by small synthetic fragments of the molecule, *Nature*, 3093):30–33.

Rhodes et al., 1986, Technetium–99m Labeling of Murine Monoclonal Antibody Fragments, *J. Nucl. Med.*, 27(5):685–693.

* cited by examiner

*Primary Examiner*—Dameron L. Jones
(74) *Attorney, Agent, or Firm*—Palmer & Dodge, LLP; Kathleen M. Williams

(57) ABSTRACT

Radioactively labeled peptides comprising oligopeptides of from 3 to 10 peptide units and containing the sequence RGD and particularly the oligopeptides RGDSY and RGDFY, are disclosed as in vivo thrombus, tumor or CAM markers for the in vivo diagnosis and detection of thrombi, tumors or CAM in mammals.

4 Claims, 1 Drawing Sheet

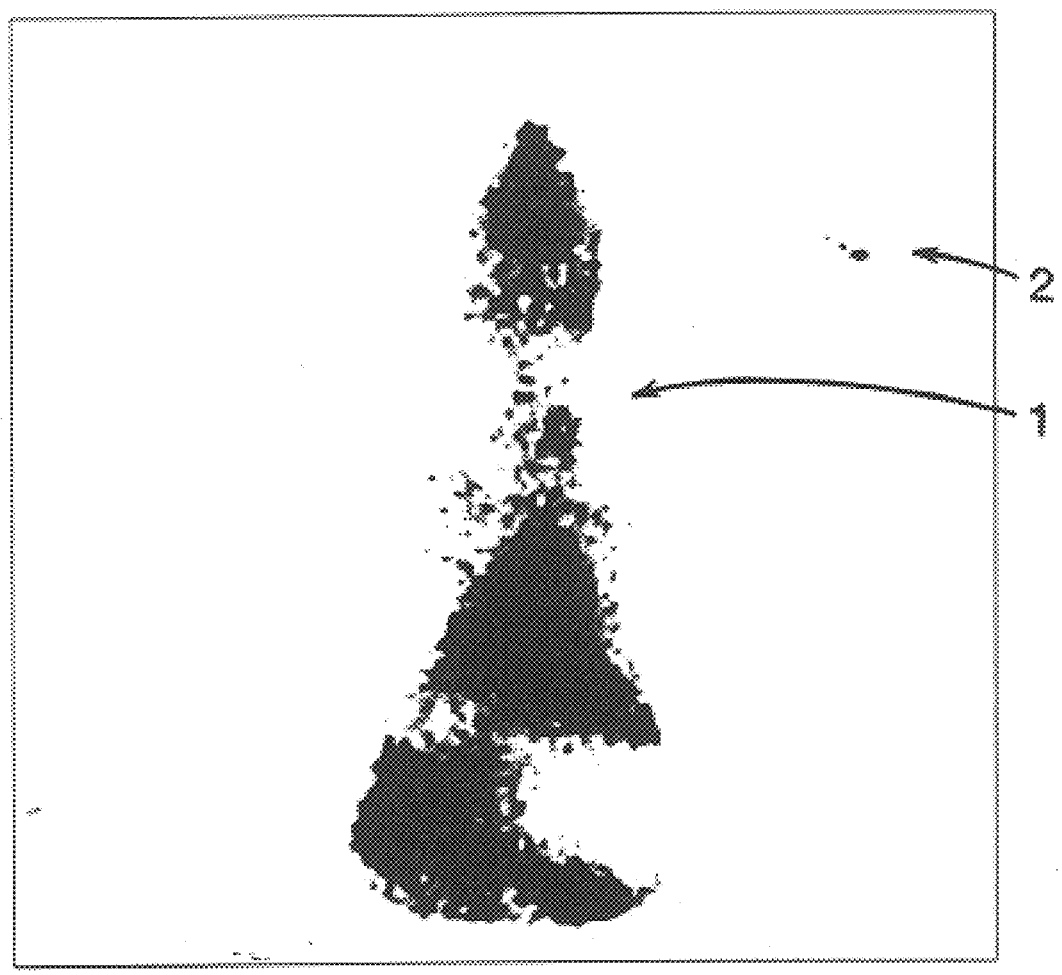

SYNTHETIC PEPTIDES FOR USE IN THROMBUS DETECTION

This application is a continuation of application Ser. No. 08/816,922, filed Mar. 12, 1997, now U.S. Pat. No. 5,843,402, which is a continuation of application Ser. No. 07/963,127, filed Oct. 19, 1992, now abandoned. This application is also a continuation of application Ser. No. 07/659,343, filed Mar. 21, 1991, now abandoned.

This invention relates to the development and use of synthetic peptides for thrombus detection both in human beings and animals, but primarily, of course, in the detection of human disease. The Method and the synthetic peptides used therein are also useful in targetting other sites in vivo, e.g., cell adhesion molecules (CAMs) and tumors, containing an RGD binding site.

In 1984 Pierschbacher and Ruoslahti (Nature, 309, 30–33), showed evidence that the cell attachment activity of fibronectin could be mimicked by small synthetic peptide fragments. The amino acid sequence responsible for this activity was shown to be Arg-Gly-Asp-Ser (RGDS) [SEQ ID NO:1] and it was demonstrated that synthetic peptides containing this sequence were able to inhibit attachment of NRK cells (cells from a neuroblastoma cell line) to fibronectin coated substrates. The inhibition obtained with RGDS [SEQ ID NO:1] containing peptides was shown to be dose-related, whilst peptides which did not contain the RGDS [SEQ ID NO:1] sequence failed to inhibit cell attachment. The serine residue of the tetrapeptide has been shown to be non-essential, although only conservative substitutions may be made in order to retain biological activity.

The RGDS [SEQ ID NO:1] sequence has been shown to occur in fibrinogen, fibronectin and von Willebrand factor. Receptors for these proteins are expressed on the platelet membrane surface following platelet activation. Cross-linking of platelets via these cytoadhesive proteins accounts for the platelet-platelet interactions within a thrombus. It has also been demonstrated that RGDS [SEQ ID NO:1] containing synthetic peptides are capable of inhibiting platelet aggregation in vitro. This would suggest a specific interaction with the GP IIb/IIIa (glycoprotein fibrinogen receptor) complex present on the platelet membrane surface, which contains the fibrinogen binding domains. Extension of the RGDS [SEQ ID NO:1] sequence, by one amino acid residue at the carboxy and amino terminal, results in a ten-fold reduction in its biological activity, although further extension is not associated with a further reduction in binding capacity. Substitution of the serine residue by phenylalanine results in an anti-aggregatory peptide which is 4 to 5 times more potent than RGDS [SEQ ID NO:1]. There has also been suggestion that the residue corresponding to serine in the RGDS [SEQ ID NO:1] sequence may impart a degree of recognition specificity for different RGDS [SEQ ID NO:1] receptors. This raises the possibility that both specificity and affinity could be modified by substitution around the RGD sequence. RGD binding sites are also known to occur on cell adhesion molecules (CAMs) and some tumors.

BRIEF DESCRIPTION OF THE FIGURE

FIG. 1 shows a radiograph taken of a rabbit following intravenous administration of a radioactively labelled peptide according to this invention, and showing the localization of the peptide in an artificially induced thrombus in the left ear.

The present invention involves a novel approach to in vivo thrombus detection and which comprises the intravenous injection into the patient (which term herein includes both humans and animals, unless the context requires otherwise) of a radioactively labelled synthetic peptide having therein an ROD (Arg-Gly-Asp)-containing sequence, preferably an RGDS [SEQ ID NO:1] (Arg-Gly-Asp-Ser) or RGDF [SEQ ID NO:2] (Arg-Gly-Asp-Phe)-containing sequence having a specific binding affinity for the platelet GP IIb/IIIa complex, and detecting the presence, If present, of the bound label on the thrombus. Present methods of thrombus detection using labelled antibodies require several hours due to the slow rate of diffusion of the antibody through the system; using labelled peptides in accordance with the present invention is expected to enable thrombus detection in a matter of minutes, thus greatly facilitating diagnosis and treatment, and at a very early stage.

For use in that method of in vivo thrombus detection there is provided in accordance with the present invention a synthetic peptide containing the sequence ROD, preferably as RGDS [SEQ ID NO:1] or RGDF [SEQ ID NO:2], and labelled with a radioactive label.

Suitable radioactive labels for use in the construction of such radioactively labelled peptides include: $Tc^{99m}$, $I^{123}$ and $In^{111}$, and will be attached to the synthetic peptide in known manner, for example, via a cystine residue in the synthetic peptide. Other suitable techniques are described in Science, 220, 613–615; Int. J. Nucl. Med. Biol., 12, 3–8; J. Nucl. Med., 27, 27, 685–693 and J. Nucl. Med., 26, 293–299.

Subject to the dictates of suitability for parenteral administration and utility, i.e. high affinity and specificity for the GP IIb/IIIa complex, the precise amino acid sequence in terms of composition and length will not be particularly critical, although for practical reasons, e.g. economy and ease of synthesis, relatively short chain peptides will be preferred containing, for example, from 3 to 10 peptide units.

Suitable peptides containing an RGD sequence, preferably an RGDS [SEQ ID NO:1] or RGDF [SEQ ID NO:2] are available from a variety of different sources, or can be manufactured quite readily using conventional peptide synthesis procedures, and, in particular, using a conventional peptide synthesiser.

Also included within the scope of this invention are a diagnostic reagent for in vivo thrombus detection comprising a parenterally administrable solution of the radioactively labelled peptide containing an RGD sequence and a parenterally administrable carrier, and a method of in vivo thrombus detection which comprises intravenously administering a radioactively labelled peptide containing and RGD sequence capable of binding to RGD binding sites on platelets in the thrombus and radiographically detecting the accumulated bound peptide.

The invention also extends to the use of the radioactively labelled peptides in in vivo localisation on to the RGD binding sites of CAMs.

Before proceeding further with the detailed description of this invention, and for the avoidance of doubt, the amino acid sequences referred to herein are identified by either their three letter abbreviations or single letter codes, as follows:

arginine=arg. or R.
aspartic acid=asp. or D.
glycine=gly. or G.
serine=ser. or S
tyrosine=tyr. or Y
phenylalanine=phe. or F
cysteine=cys. or C Reference is also made hereinafter to the accompanying figure, which is a radiograph taken of a rabbit following intravenous administration of a radioactively labelled peptide according to this invention, and showing the localisation of the peptide in an artificially induced thrombus in the left ear.

Referring to the invention in slightly more detail, studies have been conducted using four peptides (RGDSY, RGDFY [SEQ ID NO:4], RGDSYC [SEQ ID NO:5] and RGDSCRGDSY) [SEQ ID NO:6] to evaluate their potential as thrombus imaging agents.

The effect of these peptides on ADP-induced platelet aggregation was determined and compared with peptide RGDS [SEQ ID NO:1] which is known to inhibit platelet aggregation. The results (table 1) demonstrate that all four peptides studied are capable of inhibiting platelet aggregation at high concentrations and are virtually equipotent with RGDS [SEQ ID NO:1]. This suggests that inclusion of amino acids into these peptide sequences, to permit radiolabelling, does not destroy their ability to bind platelets (a prerequisite for thrombus imaging applications).

The second study involved radiodination of RGDSY [SEQ ID NO:3], RGDFY [SEQ ID NO:4], RGDSYC [SEQ ID NO:5] and RGDSCRGDSY [SEQ ID NO:6] with subsequent analysis of their ability to bind activated platelets in whole blood. The results (Table 2) indicate that all four peptides can bind platelets in ADP stimulated blood and that higher incorporation can be achieved in clotted blood.

One study was performed using RGDSY [SEQ ID NO:3], labelled with the radioisotope Iodine-123, injected into a rabbit who had a preformed thrombus in the microvasculature of the ear. The imaging studies, shown in the accompanying figure demonstrates a rapid uptake onto this thrombus (within 2 minutes of injection), which persisted for the period of study (20 minutes).

These data demonstrate that the four peptides studied are capable of binding to platelets, can be radiolabelled with gamma-emitting isotopes and are incorporated into platelet aggregates in stimulated and clotted blood. This provides good potential for thrombus detection and diagnosis by these peptides in vivo which has been confirmed, in an experimental animal model, using one of the peptides.

TABLE 1

Inhibition of ADP (1 × 10$^{-5}$M) -Induced platelet aggregation by RGDS[SEQ ID NO:1], RGDSY[SEQ ID NO:3], RGDSYC[SEQ ID NO:4], RGDSYC[SEQ ID NO:5] and RGDSCRGDSY[SEQ ID NO:6] peptides.

| | percentage inhibition | | | | |
|---|---|---|---|---|---|
| (peptide) mM | RGDS [SEQ ID NO:1] | RGDSY [SEQ ID NO:3] | RGDFY [SEQ ID NO:4] | RGDSYC [SEQ ID NO:5] | RGDSCRGDSY [SEQ ID NO:6] |
| 0.1 | 40/37 | 5/13 | 32 | 25 | 17 |
| 0.2 | 70/65 | 10/21 | 55 | — | 57 |
| 0.4 | 86/80 | 43/68 | 80 | — | 79 |

TABLE 2

Binding of radiolabelled RGDSY[SEQ ID NO:3], RGDFY[SEQ ID NO:4], RGDSYC[SEQ ID NO:5] and RGDSCRGDSY[SEQ ID NO:6] peptides ro ADP stimulated and clotted blood.

| | (bound peptide) ng | | | |
|---|---|---|---|---|
| (peptide) ng | RGDSY [SEQ ID NO:3] | RGDFY [SEQ ID NO:4] | RGDSYC [SEQ ID NO:5] | RGDSCRGDSY [SEQ ID NO:6] |
| ADP Stimulated blood | | | | |
| 1 | 0.05 | 0.01 | 0.03 | 0.01 |
| 10 | 0.64 | 1.00 | 0.94 | 0.85 |
| 100 | 9.80 | 4.46 | 9.85 | 9.07 |
| Clotted Blood | | | | |
| 1 | 0.27 | 0.41 | 0.18 | 0.28 |
| 10 | 0.85 | 2.14 | 2.26 | 2.64 |
| 100 | 17.27 | 18.12 | 27.08 | 29.33 |

The above results demonstrate the applicability of the invention over a range of synthetic peptides of different sizes all containing an RGD sequence. The actual length of the peptides is not critical, but for practical purposes the chain lengths may range from 3 to 10 peptide units, preferably 4 to 10 and, as already indicated, either consisting of or comprising an RGDS [SEQ ID NO:1] or RGDF [SEQ ID NO:2] sequence. Many such synthetic peptides are already available as known commercial products. Where not so available they can be readily synthesised by known peptide syntheses and/or using known peptide synthesisers. Similarly said synthetic peptides can be radioactively labelled by known techniques, for example, by iodination with I$^{123}$ of a terminal tyrosine (Y) unit incorporated into the peptide.

The detailed preparation of radioactively labelled peptides according to this invention is illustrated by the following example.

EXAMPLE

Preparation of Radioactively Labelled (I$^{123}$) RGDSY [SEQ ID NO:3], RGDFY [SEQ ID NO:4], RGDSYC [SEQ ID NO:5] and RGDSCRDSY [SEQ ID NO:7]

Iodogen tubes were prepared by dissolving Iodogen (1, 3, 4, 6-Tetrachloro-3α, 6α-(diphenylglycouril) in chloroform at a concentration of 1 mg.ml$^{-1}$. Aliquots of 50 μl (50 μg Iodogen) were dispensed into polypropylene cryo-tubes and the chloroform evaporated to dryness. These tubes were then stored dessicated at −20° C. until required.

Prior to radiolabelling the peptides were dissolved in phosphate buffered saline (PBS) at a concentration of 50 μg.ml$^{-1}$. RGDSYC [SEQ ID NO:5] and RGDSCRGDSY [SEQ ID NO:6] were first dissolved in a small volume of dimethyl sulphoxide (DMSO) such that the final concentration of DMSO in PBS was 1% v/v.

Iodogen tubes were equilibrated to room temperature before the addition of 200 μl peptide solution and 1–10 μl of $^{123}$I (in aqueous solution). The reation mixture was then left for 15 min at room temperature with occasional shaking. Following the incubation period the reaction mixture was removed and passed through a Sephadex G10 column which had been equilibrated with PBS. The column, which separates radiolabelled peptide from free iodine was eluted with PBS and 2 ml fractions collected. Radioactivity in the fractions was measured and the eluted peptides, represented by the first radioactive peak from the column, collected and stored at 4° C. until required.

The utility of the radioactively labelled peptides in in vivo thrombus detection is illustrated by the following experiment.

EXPERIMENT

Intravenous Administsration of Radioactively Labelled ($I^{123}$) RGDSY to Thrombitic Rabbits A male New Zealand White rabbit (3 kg) was sedated by intramuscular injection of Hypnorm (0.4 ml.kg$^{-1}$) and then anaesthetised by intravenous injection of Midazolam (2 mg.kg$^{-1}$).

Two permanent disc magnets were positioned externally in the region of the jugular vein and the rabbit was then injected with 0.2 g carbonyl iron microspheres suspended in 1 ml of contrast media (Omnipaque) via an artery of the left ear. This procedure causes microthrombi in the capillary beds of the ear, whilst iron particles passing through the ear are trapped by the magnetic field and induce thrombus formation in the jugular vein. $^{123}$I-RGDSY [SEQ ID NO:3] was injected intravenously into the contralateral ear 60 min after injection of iron. Dynamic imaging by gamma camera was performed using a 1 min frame rate for 20 min with the camera positioned anteriorly to include both ears, head and neck regions in the field of view.

Following intravenous administration of the labelled peptide, the rabbit was radiographed and the resulting radiograph is presented in the accompanying figure. As indicated by the radiograph, there was rapid uptake of the peptide by a thromus in the jugular vein (arrow 1) and by multiple tiny thrombi in the left ear (arrow 2). The latter, in particular, demonstrates the possible utility of the invention in the detection of small thrombi in vivo and the possibility of early diagnosis and treatment.

What is claimed is:

1. A method for detecting a thrombus in a patient in vivo, which comprises the steps of administering to the patient a radiolabelled peptide which binds in vivo to arginine-glycine-aspartic acid binding sites on activated platelets in the thrombus, allowing the labelled peptide to bind to the RGD binding sites on the activated platelets in the thrombus and for the unbound peptide to clear systemically from the patient, and detecting the accumulated peptide.

2. The method of claim 1, wherein the radiolabelled peptide is labelled with a radioactive substance selected from the group consisting of $^{99m}$Tc, $^{123}$I and $^{111}$In.

3. The method of claim 1, wherein the radiolabelled peptide has 3 to 10 peptide units.

4. The method of claim 1, wherein the radiolabelled peptide is a synthetic peptide.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 4 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO: 1:

Arg Gly Asp Ser
1

(2) INFORMATION FOR SEQ ID NO: 2:

(i) SEQUENCE CHARACTERISTICS:
      (A) LENGTH: 4 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO: 2:

Arg Gly Asp Phe
1

(2) INFORMATION FOR SEQ ID NO: 3:

(i) SEQUENCE CHARACTERISTICS:
      (A) LENGTH: 5 amino acids
      (B) TYPE: amino acid
      (C) STRANDEDNESS: single
      (D) TOPOLOGY: unknown (ii) MOLECULE TYPE:

(xi) SEQUENCE DESCRIPTION: SEQ ID NO: 3:

Arg Gly Asp Ser Tyr
1         5

(2) INFORMATION FOR SEQ ID NO: 4:

(i) SEQUENCE CHARACTERISTICS:
        (A) LENGTH:  5 amino acids
        (B) TYPE:    amino acid
        (C) STRANDEDNESS:  single
        (D) TOPOLOGY:  unknown (ii) MOLECULE TYPE:  peptide (xi) SEQUENCE DESCRIPTION: SEQ ID NO: 4:

Arg Gly Asp Phe Tyr
1               5

(2) INFORMATION FOR SEQ ID NO: 5:

(i) SEQUENCE CHARACTERISTICS:
        (A) LENGTH:  6 amino acids
        (B) TYPE:    amino acid
        (C) STRANDEDNESS:  single
        (D) TOPOLOGY:  unknown (ii) MOLECULE TYPE:  peptide (xi) SEQUENCE DESCRIPTION: SEQ ID NO: 5:

Arg Gly Asp Ser Tyr Cys
1               5

(2) INFORMATION FOR SEQ ID NO: 6:

(i) SEQUENCE CHARACTERISTICS:
        (A) LENGTH:  10 amino acids
        (B) TYPE:    amino acid
        (C) STRANDEDNESS:  single
        (D) TOPOLOGY:  unknown (xi) SEQUENCE DESCRIPTION: SEQ ID NO: 6:

Arg Gly Asp Ser Cys Arg Gly Asp Ser Tyr
1               5                   10

(2) INFORMATION FOR SEQ ID NO: 7:

(i) SEQUENCE CHARACTERISTICS:
        (A) LENGTH:  9 amino acids
        (B) TYPE:    amino acid
        (C) STRANDEDNESS:  single
        (D) TOPOLOGY:  unknown (ii) MOLECULE TYPE:  peptide (xi) SEQUENCE DESCRIPTION: SEQ ID NO: 7:

Arg Gly Asp Ser Cys Arg Asp Ser Tyr
1               5